United States Patent [19]

Brownell et al.

[11] 4,444,987

[45] Apr. 24, 1984

[54] METHOD OF REMOVAL OF COS FROM PROPYLENE

[75] Inventors: George L. Brownell, Monroeville Boro, Pa.; Melba J. Collier, Houston; William E. Hall, LaPorte, both of Tex.; Howard H. Morgan, Jr., Monroeville Boro; A. R. Snyder, Export Boro, both of Pa.

[73] Assignee: U.S. Steel Corporation, Pittsburgh, Pa.

[21] Appl. No.: 397,945

[22] Filed: Jul. 13, 1982

Related U.S. Application Data

[63] Continuation-in-part of Ser. No. 298,702, Sep. 1, 1981.

[51] Int. Cl.$^3$ ............... C01C 7/148; B01D 53/34
[52] U.S. Cl. ........................... 585/850; 210/749; 208/244; 423/244; 585/856; 502/31
[58] Field of Search ............... 423/244 R; 208/244; 210/749, 750; 585/850–852, 856; 502/31

[56] References Cited

U.S. PATENT DOCUMENTS

| 1,710,141 | 4/1929 | Benner et al. | 423/244 |
|---|---|---|---|
| 2,558,137 | 6/1951 | Hepp | 585/518 |
| 2,951,034 | 8/1960 | Stuart | 208/244 |
| 3,000,988 | 9/1961 | Karchmer et al. | 423/244 |
| 3,050,571 | 8/1962 | Fleming et al. | 423/244 |
| 3,058,800 | 10/1962 | Frevel et al. | 423/437 |
| 3,265,757 | 8/1966 | Frevel et al. | 585/852 |
| 3,315,003 | 4/1967 | Khelghatian | 585/809 |
| 3,456,029 | 7/1969 | Morita et al. | 585/261 |
| 3,649,169 | 3/1972 | Nicklin et al. | 423/244 |
| 3,801,669 | 4/1974 | Christmann | 585/621 |
| 3,961,035 | 6/1976 | Mickley | 423/462 |
| 4,332,781 | 6/1982 | Lieder et al. | 423/244 R |

OTHER PUBLICATIONS

Chemical Abstracts, 1978, 89/11448r.

Primary Examiner—Earl C. Thomas
Attorney, Agent, or Firm—W. Gary Goodson

[57] ABSTRACT

In a method of removing carbonyl sulfide from propylene by hydrolysis over a catalyst comprising platinum sulfide on alumina, the improvement comprising regenerating the catalyst by contacting the catalyst with a solvent for polypropylene under conditions such that any polypropylene on the catalyst will be readily dissolved. Specifically, the propylene is passed through, successively, a $C_3$-splitter, a heater, the platinum sulfide catalyst bed, and a topping still where resulting $H_2S$ and $CO_2$ are separated from the purified propylene. A preferred solvent is liquid propylene.

12 Claims, 1 Drawing Figure

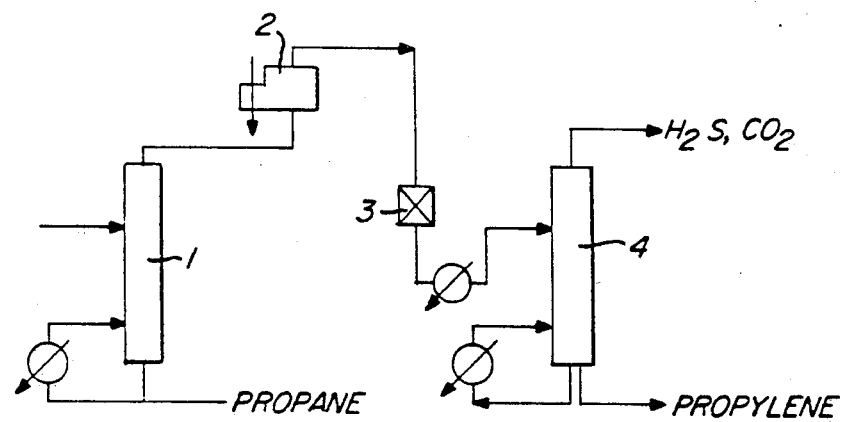

METHOD OF REMOVAL OF COS FROM PROPYLENE

This application is a continuation-in-part of patent application U.S. Ser. No. 298,702, filed Sept. 1, 1981.

BACKGROUND OF THE INVENTION

Prior to the present invention, the advent of increasingly efficient and sensitive catalysts for the polymerization of propylene has caused the polypropylene industry to recognize the importance of the control of various trace impurities in the propylene feedstock. Carbonyl sulfide has been found to be one of the most troublesome impurities, causing catalyst carryover increased ash content of product, the production of undesirable large quantities of atactic by-product, and gross inefficiencies in catalyst life and conversion rates. These difficulties tend to be more pronounced and important in proportion to the increases in yield or efficiency otherwise observed in new catalysts.

COS levels in some polypropylene feedstocks may range from an acceptable level of $\leq 50$ ppb (parts per billion by weight) to totally unacceptable levels of over 2 ppm (parts per million by weight). In the past, a solid NaOH bed has been used commercially, but NaOH alone is not capable commercially of lowering the COS concentration to $\leq 50$ ppb.

Concentrations of COS in the range of a few parts per million (e.g., 1–10 ppm) are very difficult to separate from $C_3H_6$ by fractional distillation because the boiling point of COS differs from $C_3H_6$ by only 3.4° C. Also, COS is not completely removed from propylene by the usual sulfur-removal processes such as caustic scrubbing or amine-type scrubbing due primarily to the slow rate of hydrolysis by COS.

While it is known to hydrolyze COS over a platinum sulfide-alumina catalyst, such catalysts have not been used for the hydrolysis of small amounts of COS in propylene, possibly because of the fear of deposition of polymer on the surface of the catalyst, and the difficulty of regenerating the catalyst if such a deposition occurs.

One of the serious problems that did arise was the loss of activity of the catalyst.

SUMMARY OF THE INVENTION

We have found a catalyst of platinum sulfide on alumina may be used to hydrolyze very small amounts of COS in propylene in both the liquid and gas phases provided that certain conditions are maintained. The catalyst can be regenerated to remove depositions of polymerized propylene by contacting the catalyst with a solvent for polypropylene under conditions such that polypropylene on the catalyst will be readily dissolved. Preferably, the solvent is a low-boiling hydrocarbon, with liquid propylene being most preferred.

We are able to treat propylene containing as much as 500 or more parts per million of COS to make it acceptable for use in a highly efficient ("high yield") polymerization process, i.e. to reduce the COS content to below 50 parts per billion, by passing it through a catalyst bed of platinum sulfide on alumina. For such treatment to be practical and successful, there should be present in the propylene and/or the catalyst bed a small amount of moisture, i.e. an amount of water at least double the stoichiometric amount of the COS to be hydrolyzed. The pressure may be maintained from atmospheric to about 675 psia for the liquid phase (for the vapor phase, from atmospheric to a practical limit of about 1200 psia, with about 300 psia being preferred) and the temperature for the vapor phase should be about 250° F. to 500° F. at the inlet to the catalyst vessel, although for the liquid phase the temperature can be significantly lower, i.e. 35° C. to 65° C. The flow rate of the gas will be, preferably, 1000 to 4000 SCFH (at 14.7 psia and 70° F.) of $C_3H_6$ vapor, per cubic foot of catalyst or, for liquid, preferably below 8 hr$^{-1}$.

Water may be added, usually in the form of steam, upstream of the catalyst bed.

To demonstrate our invention, certain laboratory tests were performed.

Test results obtained with PtS catalyst are summarized in Table I. The commercial catalyst contained about 0.08% platinum sulfide on an alumina support. It performed well on liquid $C_3H_6$ at space velocities of 4–5 hr$^{-1}$ (40° C.). Above 6 hr$^{-1}$ (namely, at 8 hr$^{-1}$), COS "breakthrough" occurred. The gas chromatograph analysis for COS was not sensitive below 50 ppb COS.

TABLE I
Hydrolysis of COS in Liquid Propylene on PtS/Al$_2$O$_3$ Catalyst

| Day | Temp Bed, °C. | Space Velocity, hr$^{-1}$ | COS-out ppb |
|---|---|---|---|
| 1* | 27 | 0.41[2] | <15[3] |
| 2 | 23 | 0.35 | <15 |
| 3 | 22 | 4.3 | 708 |
| 4 | 60 | 1.5 | <15 |
| 5 | 60 | 0.54 | 15 |
| 6 | 60 | 2.2 | <15 |
| 7 | 60 | 2.7 | " |
| 8 | 60 | 2.9 | " |
| 9 | 60 | 2.8 | " |
| 10 | 60 | 3.6 | " |
| 11 | 60 | 4.7 | " |
| 12 | 60 | 2.4 | " |
| 13 | 60 | 4.2 | " |
| 14 | 60 | 4.6 | " |
| 15 | 52 | 2.0 | " |
| 16 | 54 | 5.0 | " |
| 17 | 45 | 4.5 | " |
| 18 | 41 | 5.5 | " |
| 19 | 31 | 4.6 | 460 |

Test Conditions: Pressure (inlet) 450 psig
Bed Volume 65.6 ml
Feedstock - $C_3H_6$ containing 10 ppm $H_2O$ and dosed to 8.5 ppm COS;
$H_2O$ = 10 ppm

*Run time per day of 7 to 16+ hours.

Table II represents the results of an experiment in which the temperature was maintained relatively constant oveer a period of time. The catalyst was the same as used for Table I.

TABLE II

| Conditions: | Pressure - 300 psig |
|---|---|
| | Reactor Temperature - 100° F. |
| | 2–10.5 bed volumes per hour |
| Liquid Feed: | COS 10–20 ppm wt. |
| | $H_2O$ 40 ppm wt. |
| | $CH_3OH$ 150 ppm wt. |
| | $C_3H_6$ (liq.) Balance |

| Time On Stream, Hrs. | Temp., °F. | Bed Volumes per Hr. | COS ppm, wt. In | COS ppm, wt. Out | H$_2$S ppm, wt. In | H$_2$S ppm, wt. Out |
|---|---|---|---|---|---|---|
| 48 | 106 | 2.0 | 10.0 | 0.00 | 0.0 | 0.0 |
| 64 | 107 | 2.0 | 9.0 | 0.00 | 0.0 | 0.47 |
| 72 | 103 | 6.0 | 7.58 | 0.00 | 0.0 | 1.18 |
| 72.5 | 103 | 8.3 | 7.58 | 0.00 | 0.0 | 3.6 |
| 80 | 103 | 9.7 | 15.5 | 0.05 | 0.0 | 1.8 |
| 96 | 102 | 8.0 | 12.0 | 0.67 | 0.0 | 4.0 |

TABLE II-continued

| 104 | 100 | 4.0 | 11.6 | 0.00 | 0.0 | 3.8 |

A commercial-size run was conducted in the vapor phase and successfully reduced the COS in a commercial propylene to acceptable levels.

In this run, the data for COS is in terms of parts per million by volume in and parts per billion by volume out. (See Table III). The average amounts were 2.42 ppm in and 27 ppb out, or a 98.9% removal.

TABLE III

| Day | Time Hrs. | Pressure (psig) | °F. | Flow Rate (lbs/hr) | Moisture ppm | COS Feed ppm | COS Effluent ppb |
|---|---|---|---|---|---|---|---|
| 1 | 0900 | 285 | 291 | 23,400 | 82 | 4.06 | 10 |
| 2 | 0100 | 285 | 296 | 18,600 | 8.9 | 2.91 | 10 |
| 2 | 0700 | 285 | 300 | 15,600 | 3.8 | 4.47 | 25 |
| 3 | 0730 | 285 | 312 | 10,200 | 7.0 | 2.40 | 70 |
| 4 | 1430 | 280 | 281 | 15,000 | 7.7 | 1.17 | 40 |
| 5 | 0230 | 285 | 278 | 12,600 | 8.2 | 1.01 | 20 |
| 5 | 0900 | 275 | 290 | 16,200 | 7.3 | 2.47 | 20 |
| 6 | 0100 | 285 | 289 | 13,200 | 6.0 | 1.46 | 30 |
| 6 | 0830 | 280 | 290 | 16,500 | 7.0 | 2.18 | 30 |
| 6 | 1430 | 280 | 290 | 16,200 | 8.0 | 2.18 | 30 |
| 7 | 0830 | 280 | 290 | 12,600 | 7.0 | 2.22 | 20 |
| 8 | 0230 | 285 | 288 | 13,800 | 7.5 | 2.56 | 20 |

The configuration of the system used to conduct the commercial-size run is shown in the drawing. In the drawing, it may be seen that the propylene containing the COS is passed first to a "$C_3$ splitter" (1), the function of which is to remove propane from propylene which is the principal component of the incoming stream. The material is then optionally passed through a heater (2) usually in cases where it is preferred to employ a vapor phase system. If there is not enough water in the stream, it may be injected upstream of the catalyst bed, typically in the form of steam. Then the stream goes through the catalyst bed (3), converting COS to $CO_2$ and $H_2S$. The gas mixture is then conducted to the topping still (4), the function of which is to bleed off the acid gases, usually carried in a small amount of propylene. This propylene need not be lost but can be recovered by recycling to a "cracked gas" compressor or other recycling apparatus at the front end of the plant. The acid gases may be removed (together with any excess water) conveniently in a conventional scrubber or other treatment station such as an appropriate absorbent bed (e.g. ZnO) before or after the compressors. The "$C_3$ splitter" may be a conventional multi-stage distillation column designed to separate propylene/propane mixtures to produce "chemical grade" or "polymer grade" propylene as overhead products. The topping still is or may be a conventional multistage distillation column for the removal of acid gases from the product propylene. The catalyst bed is preferably a simple cylindrical vessel with an inlet at the top and an outlet at the bottom.

CATALYST REGENERATION EXAMPLE

In an experimental test in a commercial facility, a catalyst having a diameter of ⅛ inch and 0.08 weight percent platinum sulfide on an alumina support (United Catalyst Type C53-2-01) is used as described in this invention to remove COS from propylene in the vapor phase. The activity of the catalyst deteriorated as indicated by the fact than an increasingly higher temperature is required for COS removal and the fact that an increasing amount of COS is left in the propylene after passage of the gaseous propylene through the catalyst bed. To regenerate the catalyst, liquid propylene (110° F., 352 psig) is passed through the bed to wash the catalyst surface (6 bed volumes per hour, for 4 hours). When the washed bed is again put on-line, the efficiency of COS hydrolysis is improved substantially, that is, a lower bed operating temperature sufficed to reduce the COS concentration to 30 ppb. Table IV represents data for deactivated catalyst before and after regeneration. This was the first test of the regeneration mode of this invention and was conducted on Apr. 30, 1981, and required monitoring of temperature, COS concentration in and out before and after washing, as indicated in Table IV. The next test was conducted on July 31, 1981, and gave similar results.

TABLE IV

| Regeneration of Fouled Hydrolysis Content by Washing with Liquid Propylene | | | |
|---|---|---|---|
| Before Washing COS Concentration by Wt. | | After Washing COS Concentration by Wt. | |
| IN | OUT | IN | OUT |
| 3 ppm | 100 ppb | 3 ppm | 10 ppb |
| Bed Temperature to Achieve Indicated Removal - 375° F. | | Bed Temperature to Achieve Indicated Removal - 255° F. | |

An especially preferred process is the liquid phase process wherein the liquid propylene acts to continually keep the catalyst regenerated.

We claim:

1. In a method of removing carbonyl sulfide from propylene comprising passing the propylene containing carbonyl sulfide over a catalyst of platinum sulfide on alumina in the presence of water to hydrolyze the COS to $H_2S$ and $CO_2$, the improvement comprising regenerating the catalyst by contacting the catalyst with a solvent for polypropylene under conditions such that any polypropylene on the catalyst will be readily dissolved.

2. Method as in claim 1 wherein the solvent is a low boiling hydrocarbon solvent.

3. Method as in claim 1 wherein the solvent is liquid propylene.

4. Method of claim 1 conducted in the liquid phase between about 35° C. and about 65° C., and a pressure of about 200 psia to about 450 psia.

5. Method of claim 1 conducted in the vapor phase between about 135° C. and 260° C., and a pressure above atmospheric.

6. Method of claim 1 wherein the carbonyl sulfide is present in the propylene in concentrations from about 50 ppb to about 500 ppm.

7. Method of claim 1 wherein the water is present in an amount at least double the stoichiometric amount of carbonyl sulfide to be removed.

8. Method of claim 1 wherein at least some of the water is injected into the propylene.

9. In a method of removing carbonyl sulfide from propylene comprising passing the propylene containing carbonyl sulfide over a PtS/alumina catalyst in the presence of water to hydrolyze the COS to $H_2S$ and $CO_2$, and separating the $CO_2$ and $H_2S$ from the major part of the propylene by multi-stage distillation to obtain an acid gas stream containing propylene, $CO_2$ and $H_2S$, the improvement comprising regenerating the catalyst by contacting the catalyst with a solvent for polypropylene under conditions such that any polypropylene on the catalyst will be readily dissolved.

10. Method of claim 9 in which the acid gas stream is treated to remove acid gases.

11. Method of claim 10 wherein the propylene from the acid gas stream is recycled to the PtS/alumina catalyst bed.

12. Method as in claim 9 wherein the solvent is liquid propylene.

* * * * *

UNITED STATES PATENT AND TRADEMARK OFFICE
CERTIFICATE OF CORRECTION

PATENT NO. : 4,444,987

DATED : 4/24/84

INVENTOR(S) : George L. Brownell, Melba J. Collier, William E. Hall, Howard H. Morgan, Jr. and A. R. Snyder It is certified that error appears in the above-identified patent and that said Letters Patent is hereby corrected as shown below:

Column 2, line 31, in Table I, under "COS-out/ppb" column, line 5, "15" should be -- $\leq$15 --.

Signed and Sealed this

Ninth Day of October 1984

[SEAL]

Attest:

Attesting Officer

GERALD J. MOSSINGHOFF

Commissioner of Patents and Trademarks